(12) United States Patent
Iwaya et al.

(10) Patent No.: US 11,793,495 B2
(45) Date of Patent: Oct. 24, 2023

(54) ULTRASOUND ENDOSCOPE FOR SUPPRESSING IMAGE QUALITY DETERIORATION BY DIVIDING ULTRASOUND TRANSDUCERS INTO DRIVE UNITS

(71) Applicant: FUJIFILM Corporation, Tokyo (JP)

(72) Inventors: Tatsuhiro Iwaya, Ashigarakami-gun (JP); Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 149 days.

(21) Appl. No.: 17/381,874

(22) Filed: Jul. 21, 2021

(65) Prior Publication Data

US 2022/0071473 A1 Mar. 10, 2022

(30) Foreign Application Priority Data

Sep. 8, 2020 (JP) .................................. 2020-150293

(51) Int. Cl.
*A61B 1/00* (2006.01)
*A61B 8/00* (2006.01)

(52) U.S. Cl.
CPC ................ *A61B 8/56* (2013.01); *A61B 8/445* (2013.01); *A61B 8/4483* (2013.01); *A61B 2562/182* (2013.01)

(58) Field of Classification Search
CPC ......... A61B 8/56; A61B 8/445; A61B 8/4483; A61B 2562/182
See application file for complete search history.

(56) References Cited

U.S. PATENT DOCUMENTS 10,741,306 B2 * 8/2020 Kobayashi ................ B60T 8/17
2005/0165314 A1 7/2005 Tanaka
(Continued)

FOREIGN PATENT DOCUMENTS

JP 62-78909 U 5/1987
JP 2005-211096 A 8/2005
(Continued)

OTHER PUBLICATIONS

Japanese Office Action for corresponding Japanese Application No. 2020-150293, dated Mar. 20, 2023, with English translation.

*Primary Examiner* — Shahdeep Mohammed
*Assistant Examiner* — Amal Aly Farag
(74) *Attorney, Agent, or Firm* — Birch, Stewart, Kolasch & Birch, LLP (57) ABSTRACT

An ultrasound endoscope includes an insertion part including a distal end part having an ultrasound transducer array, a cable inserted into the insertion part, and a substrate, including electrode pads connected to the ultrasound transducers, respectively, that electrically connects the ultrasound transducers and the cable, and is disposed in the distal end part. The cable has a non-coaxial cable including a first cable bundle consisting of signal wires and ground wires, a first shield layer coating the first cable bundle, and an outer coat coating a second cable bundle consisting of the non-coaxial cables. Each first cable bundle is individually led out from the cable, and each signal wire is electrically connected to the corresponding electrode pad. The ultrasound transducers are configured in drive units and driven simultaneously. A signal wire group includes at least two kinds of signal wires different in length from a distal end of the first cable bundle.

10 Claims, 10 Drawing Sheets

(56) References Cited

U.S. PATENT DOCUMENTS

| | | | |
|---|---|---|---|
| 2013/0018269 A1* | 1/2013 | Matsumoto | A61B 8/4494 |
| | | | 600/459 |
| 2013/0072801 A1* | 3/2013 | Hiraoka | G10K 11/004 |
| | | | 600/463 |
| 2013/0244456 A1 | 9/2013 | Sakamoto | |
| 2013/0333917 A1 | 12/2013 | Tanabe | |
| 2014/0288334 A1 | 9/2014 | Kishi et al. | |
| 2018/0035977 A1* | 2/2018 | Wakabayashi | A61B 8/14 |
| 2019/0038257 A1 | 2/2019 | Yamamoto et al. | |
| 2019/0047021 A1 | 2/2019 | Yamamoto et al. | |
| 2019/0133559 A1 | 5/2019 | Okada et al. | |
| 2020/0205777 A1 | 7/2020 | Kumata | |

FOREIGN PATENT DOCUMENTS

| | | |
|---|---|---|
| JP | 2013-215555 A | 10/2013 |
| JP | 2019-54962 A | 4/2019 |
| WO | WO 2012/120993 A1 | 9/2012 |
| WO | WO 2013/061455 A1 | 5/2013 |
| WO | WO 2017/187755 A1 | 11/2017 |
| WO | WO 2017/187756 A1 | 11/2017 |
| WO | WO 2018/003232 A1 | 1/2018 |

\* cited by examiner

ULTRASOUND ENDOSCOPE FOR SUPPRESSING IMAGE QUALITY DETERIORATION BY DIVIDING ULTRASOUND TRANSDUCERS INTO DRIVE UNITS

CROSS-REFERENCE TO RELATED APPLICATIONS

The present application claims priority under 35 U.S.C. § 119 to Japanese Patent Application No. 2020-150293 filed on Sep. 8, 2020. The above application is hereby expressly incorporated by reference, in its entirety, into the present application.

BACKGROUND OF THE INVENTION

1. Field of the Invention

The present invention relates to an ultrasound endoscope.

2. Description of the Related Art

In recent years, an ultrasound endoscope that observes a state inside a body of a subject by irradiating the inside of the body with ultrasonic waves and receives reflected waves to capture video has been used in medical practice.

For example, as disclosed in JP2019-054962A, such an ultrasound endoscope comprises a distal end part that comprises piezoelectric elements configuring ultrasound transducers, a bending part and a flexible part connected to a proximal end of the distal end part, a plurality of coaxial cables that are inserted into the bending part and the flexible part, and a wiring substrate that electrically connects the piezoelectric elements and the coaxial cables.

SUMMARY OF THE INVENTION

Incidentally, a coaxial cable is formed by covering a shield layer and an outer coat the periphery of one signal wire coated for insulation. For this reason, the outside diameter of the coaxial cable increases, and the ultrasound endoscope is hardly reduced in diameter.

Accordingly, a case where an ultrasound endoscope is reduced in diameter by applying a non-coaxial cable instead of the coaxial cable is considered. However, in connection of a plurality of signal wires included in the non-coaxial cable and the ultrasound transducers, image quality deterioration (for example, unevenness) may occur in an ultrasound image due to the length of the signal wire.

The invention has been accomplished in view of such a situation, and an object of the invention is to provide an ultrasound endoscope capable of suppressing image quality deterioration of an ultrasound image and achieving reduction in diameter.

An ultrasound endoscope of a first aspect comprises an insertion part that includes a distal end part having an ultrasound transducer array in which a plurality of ultrasound transducers are arranged, a cable that is inserted into the insertion part, and a substrate that electrically connects the plurality of ultrasound transducers and the cable, and is disposed in the distal end part. The cable has a non-coaxial cable that includes a first cable bundle consisting of a plurality of signal wires and a plurality of ground wires, and a first shield layer with which the first cable bundle is coated, and an outer coat with which a second cable bundle consisting of a plurality of the non-coaxial cables is coated. The substrate includes a plurality of electrode pads connected to the plurality of ultrasound transducers, respectively. Each first cable bundle is individually led out from the cable, and each signal wire of the first cable bundle is led out and electrically connected to the corresponding electrode pad of the substrate. The plurality of ultrasound transducers are configured in a plurality of drive units to be driven simultaneously. The plurality of signal wires of each first cable bundle are connected to a plurality of the electrode pads in each drive unit to configure a signal wire group, and the signal wire group includes at least two kinds or more of signal wires different in length from a distal end of the first cable bundle.

In an ultrasound endoscope of a second aspect, in the signal wire group, the signal wires in each first cable bundle have an equal length, and the signal wires have two kinds or more of lengths between the first cable bundles.

In an ultrasound endoscope of a third aspect, in the signal wire group, the signal wires in each first cable bundle have two kinds or more of different lengths.

In an ultrasound endoscope of a fourth aspect, all the signal wires in each first cable bundle have different lengths.

In an ultrasound endoscope of a fifth aspect, the signal wire group includes at least one signal wire having a different length.

In an ultrasound endoscope of a sixth aspect, the cable includes a second shield layer with which the second cable bundle is coated, inside the outer coat.

In an ultrasound endoscope of a seventh aspect, the cable includes a resin layer with which the second cable bundle is coated, between the second cable bundle and the second shield layer.

In an ultrasound endoscope of an eighth aspect, the cable includes a resin layer with which the second cable bundle is coated, inside the outer coat.

In an ultrasound endoscope of a ninth aspect, the resin layer is a fluorine-based resin layer.

With the ultrasound endoscope according to the aspects of the invention, it is possible to suppress image quality deterioration of an ultrasound image and to achieve reduction in diameter.

DESCRIPTION OF THE PREFERRED EMBODIMENTS

Hereinafter, a preferred embodiment of an ultrasound endoscope according to the invention will be described referring to the accompanying drawings.

Figure 1:
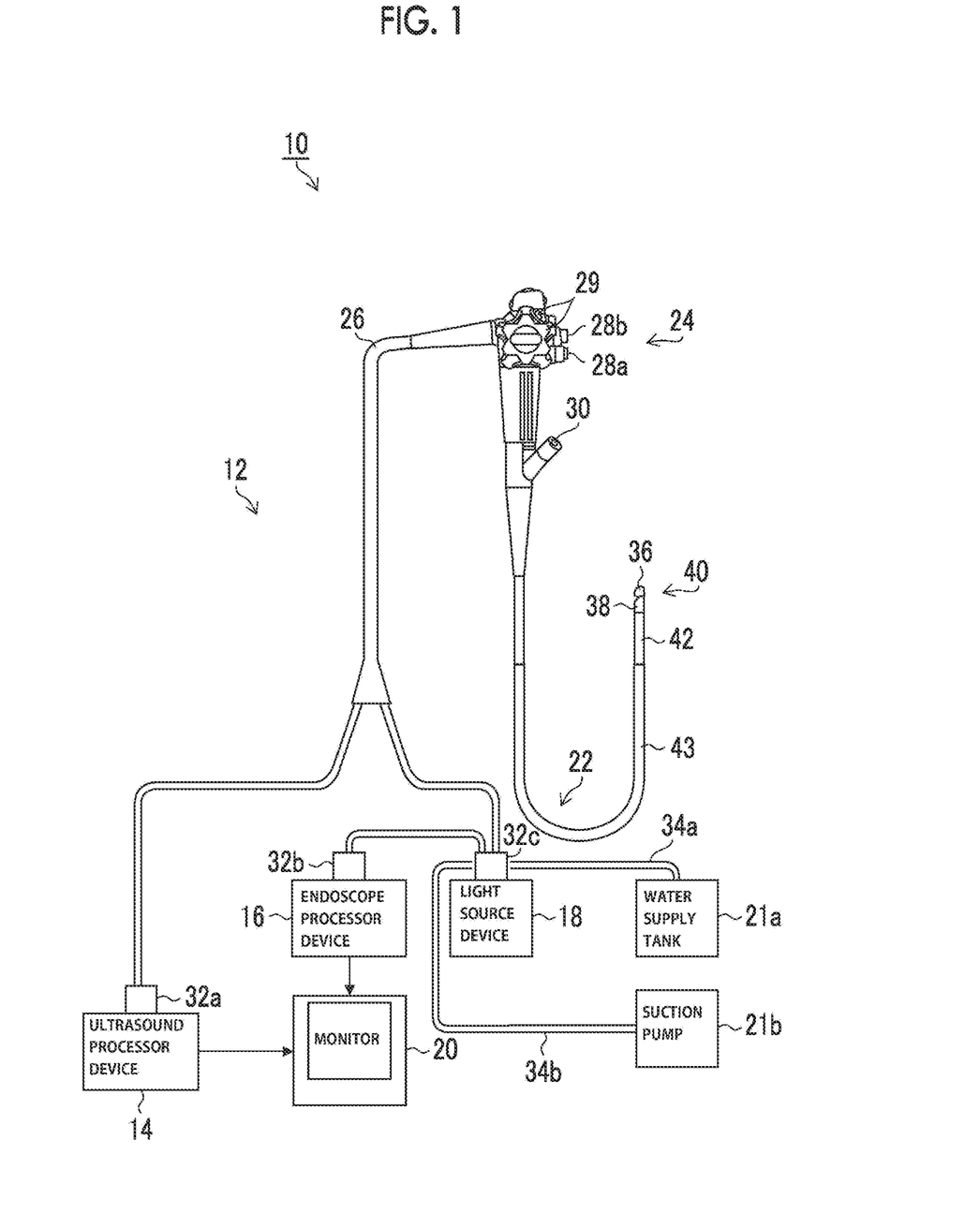
FIG. 1 is a schematic configuration diagram showing an example of the configuration of an ultrasonography system.

FIG. 1 is a schematic configuration diagram showing an example of an ultrasonography system 10 that uses an ultrasound endoscope 12 of an embodiment.

As shown in FIG. 1, the ultrasonography system 10 comprises an ultrasound endoscope 12, an ultrasound processor device 14 that generates an ultrasound image, an endoscope processor device 16 that generates an endoscope image, a light source device 18 that supplies illumination light, with which the inside of a body cavity is illuminated, to the ultrasound endoscope 12, and a monitor 20 that displays the ultrasound image and the endoscope image. The ultrasonography system 10 comprises a water supply tank 21a that stores cleaning water or the like, and a suction pump 21b that sucks aspirates inside the body cavity.

The ultrasound endoscope 12 has an insertion part 22 that is inserted into the body cavity of the subject, an operating part 24 that is consecutively provided in a proximal end portion of the insertion part 22 and is used by an operator to perform an operation, and a universal cord 26 that has one end connected to the operating part 24.

In the operating part 24, an air and water supply button 28a that opens and closes an air and water supply pipe line (not shown) from the water supply tank 21a, and a suction button 28b that opens and closes a suction pipe line (not shown) from the suction pump 21b are provided side by side. In the operating part 24, a pair of angle knobs 29 and 29 and a treatment tool insertion port 30 are provided.

In the other end portion of the universal cord 26, an ultrasound connector 32a that is connected to the ultrasound processor device 14, an endoscope connector 32b that is connected to the endoscope processor device 16, and a light source connector 32c that is connected to the light source device 18 are provided. The ultrasound endoscope 12 are attachably and detachably connected to the ultrasound processor device 14, the endoscope processor device 16, and the light source device 18 respectively through the connectors 32a, 32b, and 32c. The connector 32c comprises an air and water supply tube 34a that is connected to the water supply tank 21a, and a suction tube 34b that is connected to the suction pump 21b.

The insertion part 22 has, in order from a distal end side, a distal end part 40 having an ultrasound observation part 36 and an endoscope observation part 38, a bending part 42 that is consecutively provided on a proximal end side of the distal end part 40, and a flexible part 43 that couples a proximal end side of the bending part 42 and the distal end side of the operating part 24.

The bending part 42 is remotely bent and operated by rotationally moving and operating a pair of angle knobs 29 and 29 provided in the operating part 24. With this, the distal end part 40 can be directed in a desired direction.

The ultrasound processor device 14 generates and supplies an ultrasound signal for making an ultrasound transducer array 50 of an ultrasound transducer unit 46 (see FIG. 2) of an ultrasound observation part 36 described below generate an ultrasonic wave. The ultrasound processor device 14 receives and acquires an echo signal reflected from an observation target part irradiated with the ultrasonic wave, by the ultrasound transducer array 50 and executes various kinds of signal processing on the acquired echo signal to generate an ultrasound image that is displayed on the monitor 20.

The endoscope processor device 16 receives and acquires a captured image signal acquired from the observation target part illuminated with illumination light from the light source device 18 in the endoscope observation part 38 and execute various kinds of signal processing and image processing on the acquired image signal to generate an endoscope image that is displayed on the monitor 20.

The ultrasound processor device 14 and the endoscope processor device 16 are configured with two devices (computers) provided separately. Note that the invention is not limited thereto, and both the ultrasound processor device 14 and the endoscope processor device 16 may be configured with one device.

To image an observation target part inside a body cavity using the endoscope observation part 38 to acquire an image signal, the light source device 18 generates illumination light, such as white light including light of three primary colors of red light, green light, and blue light or light of a specific wavelength. Light propagates through a light guide (not shown) and the like in the ultrasound endoscope 12, and is emitted from the endoscope observation part 38, and the observation target part inside the body cavity is illuminated with light.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

Next, the configuration of the distal end part 40 will be described referring to FIGS. 2 to 4.

Figure 2:
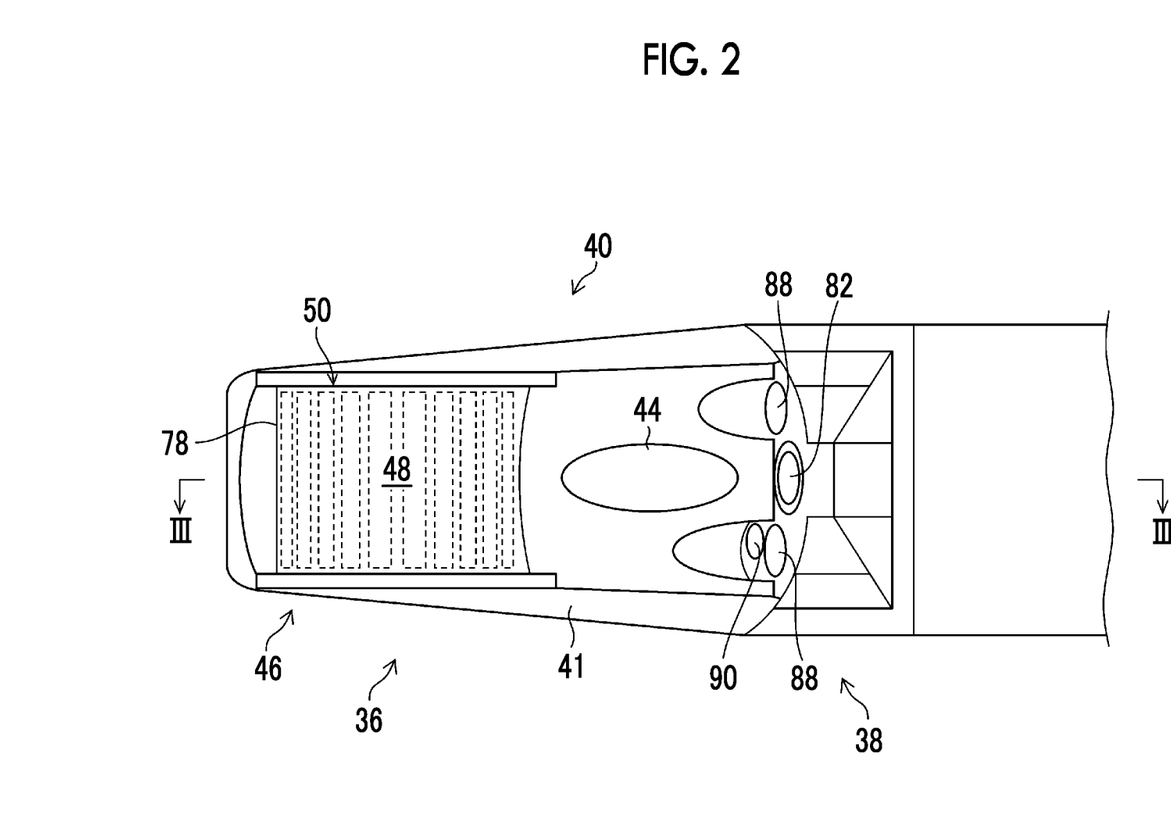
FIG. 2 is a partial enlarged plan view showing a distal end part of an ultrasound endoscope of FIG. 1 and the vicinity of the distal end part.

FIG. 2 is a partial enlarged plan view showing the distal end part 40 shown in FIG. 1 and the vicinity thereof the distal end part 40. FIG. 3 is a cross-sectional view taken along the line shown in FIG. 2, and is a longitudinal sectional view of the distal end part 40 taken along a center line thereof in a longitudinal axis direction. FIG. 4 is a cross-sectional view taken along the line Iv-Iv shown in FIG. 3, and is a cross-sectional view of the ultrasound transducer array 50 of the ultrasound observation part 36 of the distal end part 40 taken along a center line of an arc structure.

Figure 3:
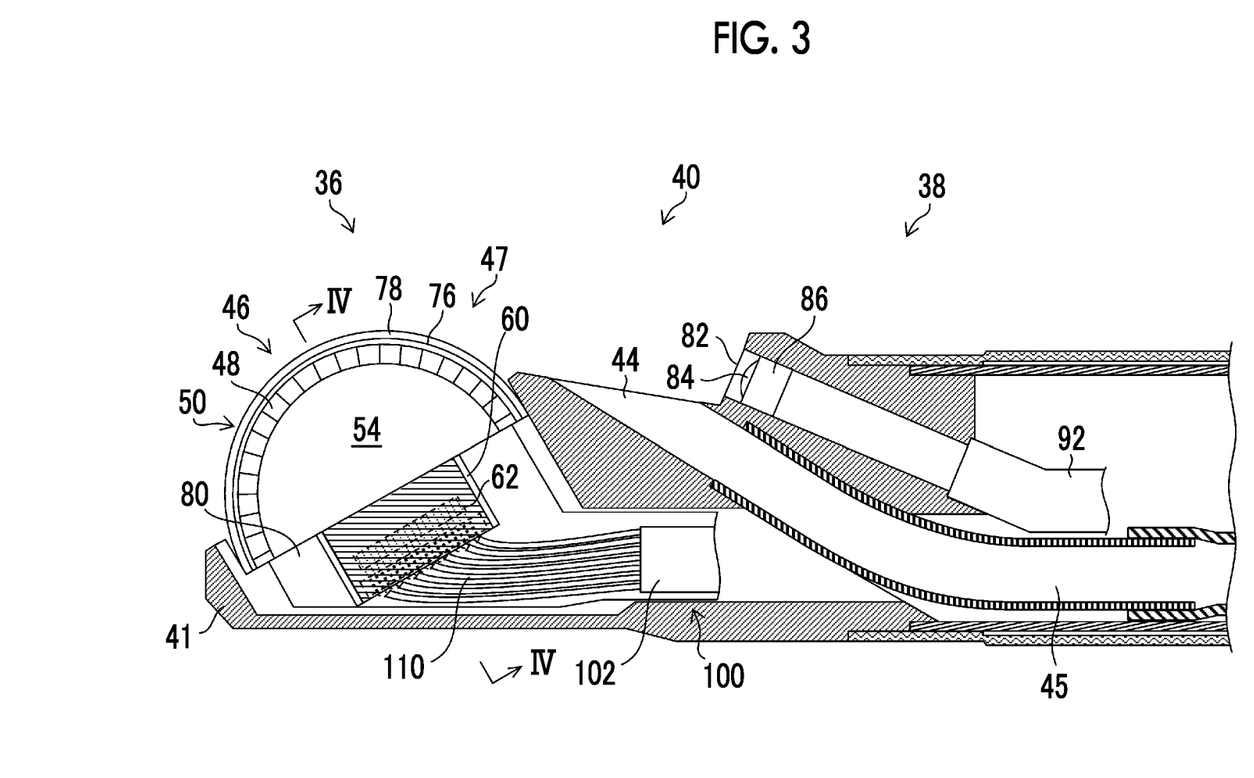
FIG. 3 is a cross-sectional view taken along the line III-III of FIG. 2.

As shown in FIGS. 2 and 3, in the distal end part 40, the ultrasound observation part 36 that acquires an ultrasound image is mounted on the distal end side, and the endoscope observation part 38 that acquires an endoscope image is mounted on the proximal end side. In the distal end part 40, a treatment tool lead-out port 44 is provided between the ultrasound observation part 36 and the endoscope observation part 38.

The endoscope observation part 38 is configured with an observation window 82, an objective lens 84, a solid-state imaging element 86, illumination windows 88, a cleaning nozzle 90, a wiring cable 92, and the like.

The treatment tool lead-out port 44 is connected to a treatment tool channel 45 that is inserted into the insertion part 22. A treatment tool (not shown) inserted from the treatment tool insertion port 30 of FIG. 1 is let out from the treatment tool lead-out port 44 into the body cavity through the treatment tool channel 45.

Figure 4:
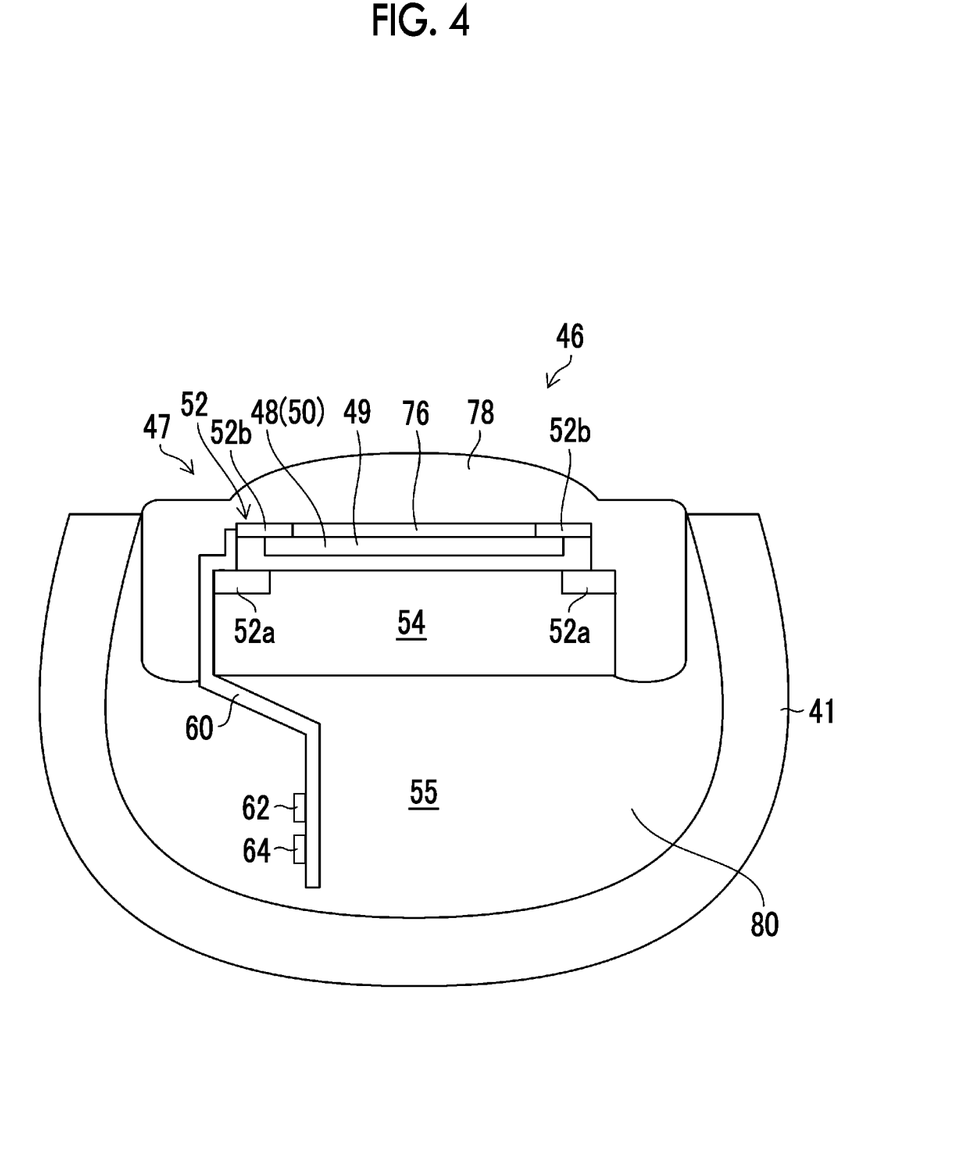
FIG. 4 is a cross-sectional view taken along the line IV-IV shown in FIG. 3.

As shown in FIGS. 2 to 4, the ultrasound observation part 36 comprises the ultrasound transducer unit 46, an exterior member 41 that holds the ultrasound transducer unit 46, and a cable 100 that is electrically connected to the ultrasound transducer unit 46 through a substrate 60. The exterior member 41 is made of a rigid member, such as rigid resin, and configures a part of the distal end part 40.

The ultrasound transducer unit 46 has the ultrasound transducer array 50 that consists of a plurality of ultrasound transducers 48, an electrode 52 that is provided on an end side of the ultrasound transducer array 50 in a width direction (a direction perpendicular to the longitudinal axis direction of the insertion part 22), a backing material layer 54 that supports each ultrasound transducer 48 from a lower surface side, the substrate 60 that is disposed along a side surface of the backing material layer 54 in the width direction and is connected to the electrode 52, and a filler layer 80 with which an internal space 55 between the exterior member 41 and the backing material layer 54 is filled.

As long as the substrate 60 can electrically connect a plurality of ultrasound transducers 48 and the cable 100, in particular, the structure thereof is not limited.

It is preferable that the substrate 60 is configured with, for example, a wiring substrate, such as a flexible substrate (flexible print substrate (also referred to as a flexible printed circuit (FPC)) having flexibility, a printed wiring circuit substrate (also referred to as a printed circuit board (PCB)) made of a rigid substrate having high rigidity with no flexibility, or a printed wiring substrate (also referred to as a printed wired board (PWB)).

The ultrasound transducer unit 46 has an acoustic matching layer 76 laminated on the ultrasound transducer array 50, and an acoustic lens 78 laminated on the acoustic matching layer 76. That is, the ultrasound transducer unit 46 is configured as a laminate 47 having the acoustic lens 78, the acoustic matching layer 76, the ultrasound transducer array 50, and the backing material layer 54.

The ultrasound transducer array 50 is configured with a plurality of rectangular parallelepiped ultrasound transducers 48 arranged in a convex arc shape outward. The ultrasound transducer array 50 is an array of 48 to 192 channels including 48 to 192 ultrasound transducers 48, for example. Each of the ultrasound transducer 48 has a piezoelectric body 49.

The ultrasound transducer array 50 has the electrode 52. The electrode 52 has an individual electrode 52a individually and independently provided for each ultrasound transducer 48, and a transducer ground 52b that is a common electrode common to all the ultrasound transducers 48. In FIG. 4, a plurality of individual electrodes 52a are disposed on lower surfaces of end portions of a plurality of ultrasound transducers 48, and the transducer ground 52b is disposed on upper surfaces of the end portions of the ultrasound transducers 48.

The substrate 60 has 48 to 192 wirings (not shown) that are electrically connected to the individual electrodes 52a of the 48 to 192 ultrasound transducers 48, respectively, and a plurality of electrode pads 62 that are connected to the ultrasound transducers 48 through the wirings, respectively.

The ultrasound transducer array 50 has a configuration in which a plurality of ultrasound transducers 48 are arranged at a predetermined pitch in a one-dimensional array as an example. The ultrasound transducers 48 configuring the ultrasound transducer array 50 are arranged at regular intervals in a convex bent shape along an axial direction of the distal end part 40 (the longitudinal axis direction of the insertion part 22) and are sequentially driven based on drive signals input from the ultrasound processor device 14 (see FIG. 1). With this, convex electronic scanning is performed with a range where the ultrasound transducers 48 shown in FIG. 2 are arranged, as a scanning range.

The acoustic matching layer 76 is a layer that is provided for taking acoustic impedance matching between the subject and the ultrasound transducers 48.

The acoustic lens 78 is a lens that is provided for converging the ultrasonic waves emitted from the ultrasound transducer array 50 toward the observation target part. The acoustic lens 78 is formed of, for example, silicon-based resin (millable type silicon rubber, liquid silicon rubber, or the lie), butadiene-based resin, or polyurethane-based resin. In the acoustic lens 78, powder, such as titanium oxide, alumina, or silica, is mixed as necessary. With this, the acoustic lens 78 can take acoustic impedance matching between the subject and the ultrasound transducers 48 in the acoustic matching layer 76, and can increase the transmittance of the ultrasonic waves.

As shown in FIGS. 3 and 4, the backing material layer 54 is disposed on an inside with respect to the arrangement surface of a plurality of ultrasound transducers 48, that is, a rear surface (lower surface) of the ultrasound transducer array 50. The backing material layer 54 is made of a layer of a member made of a backing material. The backing material layer 54 has a role of mechanically and flexibly supporting the ultrasound transducer array 50 and attenuating ultrasonic waves propagated to the backing material layer 54 side among ultrasound signals emitted from a plurality of ultrasound transducers 48 or reflected propagated from the observation target. For this reason, the backing material is made of a material having rigidity, such as hard rubber, and an ultrasonic wave attenuation material (ferrite, ceramics, or the like) is added as needed.

The filler layer 80 is a layer with which the internal space 55 between the exterior member 41 and the backing material layer 54 is filled, and has a role of fixing the substrate 60, the non-coaxial cables 110, and various wiring portions. It is preferable that the acoustic impedance of the filler layer 80 matches the acoustic impedance of the backing material layer 54 with given accuracy or higher such that the ultrasound signals propagated from the ultrasound transducer array 50 to the backing material layer 54 side are not reflected at a boundary surface between the filler layer 80 and the backing material layer 54. It is preferable that the filler layer 80 is made of a member having heat dissipation to increase efficiency in dissipating heat generated in a plurality of ultrasound transducers 48. In a case where the filler layer 80 has heat dissipation, heat is received from the backing material layer 54, the substrate 60, the non-coaxial cables 110, and the like, and thus, heat dissipation efficiency can be improved.

With the ultrasound transducer unit 46 configured as described above, in a case where each ultrasound transducer 48 of the ultrasound transducer array 50 is driven, and a voltage is applied to the electrode 52 of the ultrasound transducer 48, the piezoelectric body 49 vibrates to sequentially generate ultrasonic waves, and the irradiation of the ultrasonic waves is performed toward the observation target part of the subject. Then, as a plurality of ultrasound transducers 48 are sequentially driven by an electronic switch, such as a multiplexer, scanning with ultrasonic waves is performed in a scanning range along a curved surface on which the ultrasound transducer array 50 is disposed, for example, a range of about several tens mm from the center of curvature of the curved surface.

In a case where the echo signal reflected from the observation target part is received, the piezoelectric body 49 vibrates to generate a voltage and outputs the voltage as an electric signal corresponding to the received ultrasound echo to the ultrasound processor device 14. Then, the electric signal is subjected to various kinds of signal processing in the ultrasound processor device 14 and is displayed as an ultrasound image on the monitor 20.

In the embodiment, the substrate 60 shown in FIG. 4 has, at one end, a plurality of electrode pads 62 that are electrically connected to a plurality of individual electrodes 52*a*, and a ground electrode pad 64 that is electrically connected to the transducer ground 52*b*. In FIG. 4, the cable 100 is omitted.

Electrical bonding of the substrate 60 and the individual electrodes 52*a* can be established by, for example, a resin material having conductivity. Examples of the resin material include an anisotropic conductive film (ACF) or an anisotropic conductive paste (ACP) obtained by mixing thermosetting resin with fine conductive particles and forming the mixture into a film.

As another resin material, for example, a resin material in which a conductive filler, such as metallic particles, is dispersed into binder resin, such as epoxy or urethane, and the filler forms a conductive path after adhesion may be used. Examples of this resin material include a conductive paste, such as a silver paste.

As shown in FIG. 3, the cable 100 comprises a plurality of non-coaxial cables 110, and an outer coat 102 with which a plurality of non-coaxial cables 110 are coated. Signal wires included in the non-coaxial cable 110 are electrically bonded to the electrode pads 62 of the substrate 60.

Next, a connection structure of the substrate 60 and the cable 100 will be described referring to the drawings.

Figure 5:
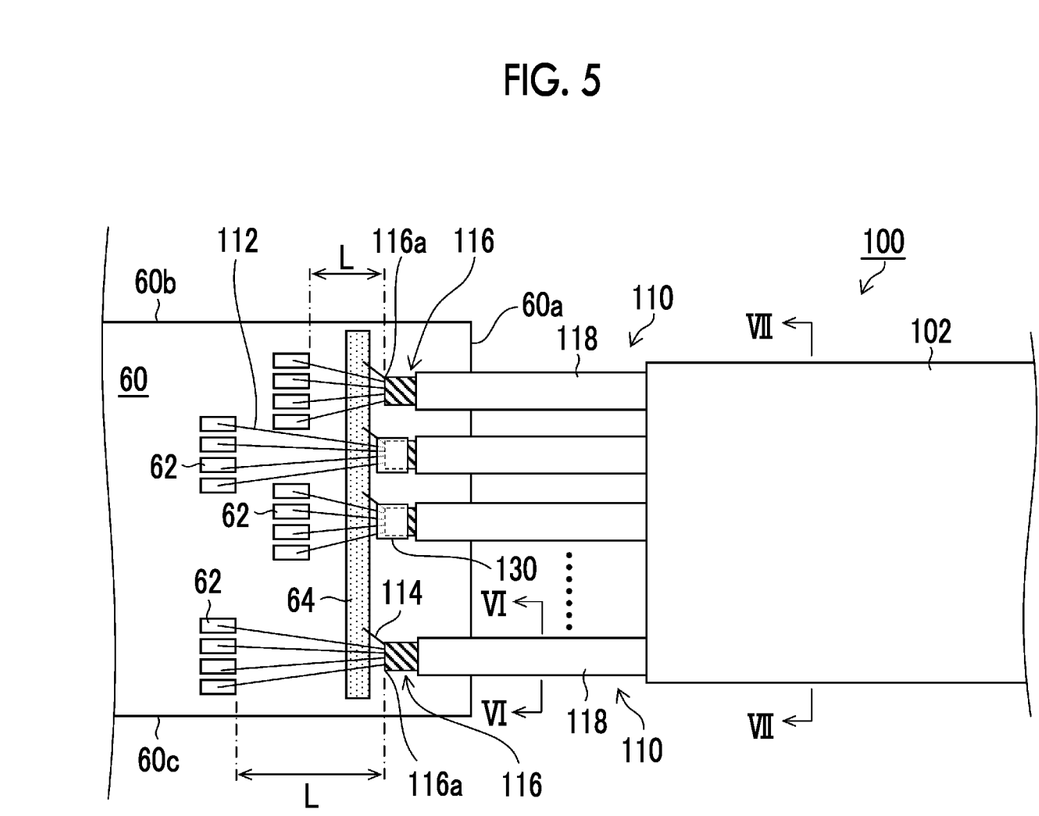
FIG. 5 is a diagram showing a connection structure of a substrate and non-coaxial cables.
Figure 6:
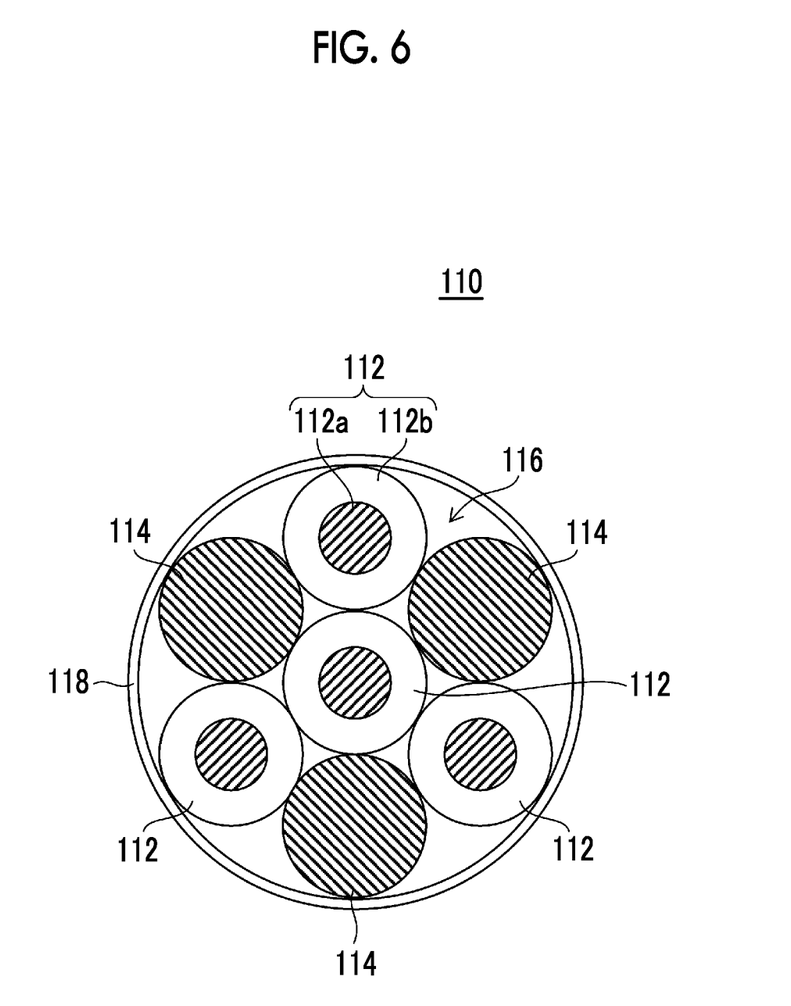
FIG. 6 is a cross-sectional view of a non-coaxial cable taken along the line VI-VI of FIG. 5.
Figure 7:
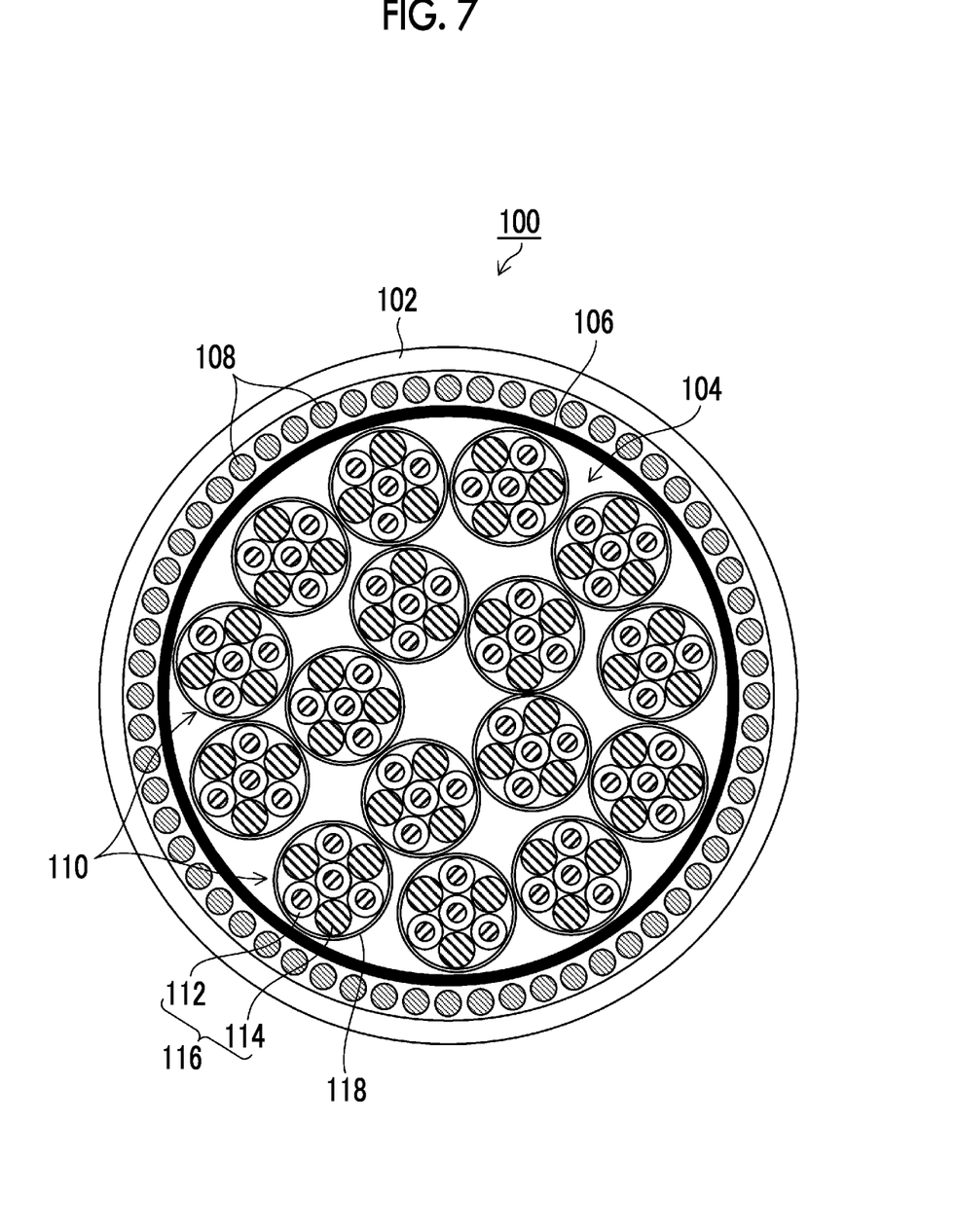
FIG. 7 is a cross-sectional view of a cable taken along the line VII-VII of FIG. 5.

FIG. 5 is an enlarged view of a portion including the substrate 60 and the cable 100. FIG. 6 is a cross-sectional view taken along the line VI-VI. FIG. 7 is a cross-sectional view taken along the line VII-VII.

As shown in FIG. 5, the substrate 60 has a plurality of electrode pads 62 disposed along a side 60*a* on a proximal end side, and the ground electrode pad 64 disposed between a plurality of electrode pads 62 and the side 60*a*. The ground electrode pad 64 is disposed in parallel to the side 60*a*.

The cable 100 is disposed at a position facing the side 60*a* of the substrate 60. The cable 100 comprises a plurality of non-coaxial cables 110, and the outer coat 102 that covers a plurality of non-coaxial cables 110. The electrode pads 62 and signal wires 112 of the non-coaxial cables 110 are electrically bonded. The non-coaxial cables 110 are disposed in parallel with a side 60*b* and a side 60*c* perpendicular to the side 60*a*. Note that a positional relationship between the substrate 60 and the non-coaxial cables 110 is not particularly limited.

Next, the structure of the non-coaxial cables 110 will be described. As shown in FIG. 6, each non-coaxial cable 110 has a plurality of signal wires 112 and a plurality of ground wires 114. Each signal wire 112 is made of, for example, a conductor 112*a*, and an insulating layer 112*b* with which the periphery of the conductor 112*a* is coated. The conductor 112*a* is made of, for example, an element wire, such as copper or copper alloy. The element wire is subjected to, for example, plating processing, such as tin plating or silver plating. The conductor 112*a* has a diameter of 0.03 mm to 0.04 mm.

The insulating layer 112*b* can be made of, for example, a resin material, such as fluorinated-ethylene-propylene (FEP) or perfluoroalkoxy (PFA). The insulating layer 112*b* has a thickness of 0.015 mm to 0.025 mm.

Each ground wire 114 is made of a conductor having the same diameter as the signal wire 112. The ground wire 114 is made of an element wire, such as copper or copper alloy, or a stranded wire obtained by stranding a plurality of element wires, such as copper or copper alloy.

A first cable bundle 116 is configured by stranding a plurality of signal wires 112 and a plurality of ground wires 114.

Each non-coaxial cable 110 comprises a first shield layer 118 with which the periphery of the first cable bundle 116 is coated. The first shield layer 118 can be made of an insulating film obtained by laminating metallic foils through an adhesive. The insulating film is made of a polyethylene terephthalate (PET) film. The metallic foil is made of an aluminum foil or a copper foil.

The non-coaxial cable 110 is shielded by the first shield layer 118 with a plurality of signal wires 112 as one set. The signal wires 112 are handled in a unit of the non-coaxial cable 110.

As shown in FIG. 6, in the non-coaxial cable 110 of the embodiment, the first cable bundle 116 is configured by stranding seven wires in total of four signal wires 112 and three ground wires. One signal wire 112 of the four signal wires 112 is disposed at the center. The remaining three signal wires 112 and the three ground wires 114 are disposed adjacently in the periphery of the signal wire 112 at the center. Note that the number of signal wires 112, the number of ground wires 114, and the disposition of the wires in the first cable bundle 116 are not limited to the structure of FIG. 6.

Next, the structure of the cable 100 will be described. As shown in FIG. 7, the cable 100 comprises a plurality of non-coaxial cables 110. A second cable bundle 104 is configured with a plurality of non-coaxial cables 110.

The second cable bundle 104 is coated with the outer coat 102. The outer coat 102 can be made of a fluorine-based resin material, such as extruded and coated PFA, FEP, an ethylene/ethylene tetrafluoride copolymer (ETFE), or polyvinyl chloride (PVC). The outer coat 102 can be made of a wound resin tape (PET tape). The coating of the second cable bundle 104 with the outer coat 102 includes a case where the outside of the second cable bundle 104 is coated directly and a case where the outside of the second cable bundle 104 is coated indirectly. Indirect coating includes disposing another layer between the outer coat 102 and the second cable bundle 104.

The cable 100 of the embodiment comprises, in order from the inside, a resin layer 106 and a second shield layer 108 between the outer coat 102 and the second cable bundle 104. The second cable bundle 104 is coated with the resin layer 106. The resin layer 106 can be made of, for example, the fluorine-based resin material or the resin tape described above.

The second shield layer 108 may be configured by, for example, braiding a plurality of element wires. The element wire is made of a copper wire, a copper alloy wire, or the like subjected to plating processing (tin plating or silver plating).

The cable 100 may not comprise both the resin layer 106 and the second shield layer 108 other than the above-described configuration or may comprise only one of the resin layer 106 or the second shield layer 108.

The cable 100 of the embodiment includes 16 non-coaxial cables 110, and includes 64 signal wires 112. The number of non-coaxial cables 110 and the number of signal wires 112 are not limited to the numerical values.

As described above, the non-coaxial cable 110 included in the cable 100 does not comprise a shield layer and an outer coat for each signal wire 112, unlike the coaxial cable in the related art. In particular, in a case where the cable 100 is configured with a plurality of non-coaxial cables 110, the cable 100 can be reduced in diameter compared to the coaxial cable in the related art. In a case where the outside diameter is the same as the outside diameter of the coaxial cable, the cable 100 can comprise a greater number of signal wires 112 than the coaxial cable in the related art.

Next, a connection structure of the substrate 60 and the non-coaxial cables 110 will be described in detail. As shown in FIG. 5, on the proximal end side of the substrate 60, the resin layer 106 (not shown), the second shield layer 108 (not shown), and the outer coat 102 of the cable 100 are removed, and a plurality of non-coaxial cables 110 are exposed. On the proximal end side of the substrate 60, the first shield layer 118 of each non-coaxial cable 110 is removed, and the first cable bundle 116 is exposed.

The first shield layer 118 is positioned on the substrate 60, and the substrate 60 and the first shield layer 118 overlap at least partially as viewed from a direction perpendicular to a principal surface of the substrate 60 (hereinafter, in plan view). The first cable bundle 116 is exposed only on the substrate 60, and the substrate 60 and the first cable bundle 116 overlap only on the substrate 60. The first cable bundle 116 does not protrude from the substrate 60, and thus, the whole first cable bundle 116 is superimposed on the substrate 60.

The substrate 60 and the first cable bundle 116 are fixed by a fixing part 130, and the relative positions of the substrate 60 and each first cable bundle 116 are fixed. The fixing part 130 fixes the substrate 60 and the first cable bundle 116 in a state overlapping the substrate 60. The first cable bundle 116 configured with a stranded wire of a plurality of signal wires 112 and a plurality of ground wires 114 is unstranded into the respective signal wires 112 at a distal end 116a. Each unstranded signal wire 112 is electrically bonded to the electrode pad 62 disposed on the substrate 60. The distal end 116a is a start position where each signal wire 112 is unstranded. In some first cable bundles 116, the fixing part 130 is omitted for ease of understanding.

As described above, each signal wire 112 of the non-coaxial cable 110 is configured with the conductor 112a and the insulating layer 112b, and a shield layer is not provided for each signal wire 112, unlike a coaxial cable. For this reason, the signal wires 112 are likely to be disconnected at the time of a wiring work of electrically bonding the electrode pads 62 and the signal wires 112, subsequent handling, and an assembling step to the probe.

In the embodiment, preferably, the substrate 60 and the first cable bundle 116 are fixed by the fixing part 130. Accordingly, when stress is applied to the cable 100 or the non-coaxial cable 110, stress is prevented from being transmitted to a bonded portion of the electrode pad 62 and the signal wire 112, and disconnection of the signal wire 112 can be prevented.

The fixing part 130 is not particularly limited as long as the relative positional relationship between the substrate 60 and the first cable bundle 116 can be fixed, and for example, any one of an adhesive, solder, or a clamp member, or a combination thereof can be applied. The fixing part 130 can individually fix the substrate 60 and the first cable bundle 116 or can fix the substrate 60 and a plurality of first cable bundles 116 in a lump.

The ground wires 114 of each first cable bundle 116 are electrically bonded to the ground electrode pad 64 of the substrate 60. At least one ground wire 114 included in each first cable bundle 116 is electrically bonded to the ground electrode pad 64. A plurality of ground wires 114 are in contact with each other in the first cable bundle 116. Accordingly, at least one ground wire 114 of each first cable bundle 116 is electrically bonded to the ground electrode pad 64, where the ground potentials of a plurality of first cable bundles 116 can be at the same potential. A region occupied by the wires can be reduced by reducing the number of ground wires 114 that are electrically bonded to the ground electrode pad 64. As a result, it is possible to achieve reduction in diameter of the distal end part 40.

In the connection structure shown in FIG. 5, the electrode pads 62 corresponding to each non-coaxial cable 110 are collectively disposed. That is, four electrode pads 62 that are electrically bonded to the four signal wires 112 are collectively disposed on the substrate 60. It is preferable that the electrode pads 62 corresponding to the non-coaxial cable 110 are the electrode pads 62 that are disposed in an extension direction of the non-coaxial cable 110. It is preferable that the signal wires 112 of each non-coaxial cable 110 are not electrically bonded to the electrode pads 62 of an adjacent non-coaxial cable 110. It is possible to prevent stress from being applied to the signal wires 112.

In the connection structure shown in FIG. 5, the positions of the electrode pads 62 connected to the signal wires 112 of the non-coaxial cable 110 are different between adjacent non-coaxial cables 110. In comparison of the electrode pads 62 corresponding to the non-coaxial cable 110 closest to the side 60b with the electrode pads 62 corresponding to the non-coaxial cable 110 second closest to the side 60b, a distance L from the distal end 116a of the first cable bundle 116 fixed by the fixing part 130 is different. There are two kinds of distances L different between the first cable bundles 116.

As a result, a plurality of electrode pads 62 corresponding to the signal wires 112 of the non-coaxial cable 110 are disposed in zigzags for every plurality of electrode pads 62 in plan view. It is possible to narrow an interval between a plurality of adjacent electrode pads 62, and to dispose a plurality of electrode pads 62 with high density compared to a case where a plurality of electrode pads 62 are not disposed in zigzags (a case where a plurality of electrode pads 62 are disposed linearly along the side 60a).

In the embodiment, although the two kinds of distances L are shown, two kinds or more of distances L can be set. It is possible to dispose a plurality of electrode pads 62 with higher density.

The lengths of the signal wires 112 are different between the first cable bundles 116 of the non-coaxial cables 110 corresponding to the electrode pads 62 disposed in zigzags.

On the other hand, in a unit of the non-coaxial cables 110, the distance L between the electrode pads 62 corresponding to a plurality of signal wires 112 and the distal end 116a of the first cable bundle 116 are equal.

Next, a first embodiment of a connection relationship between a plurality of ultrasound transducers 48 and a plurality of non-coaxial cables 110 will be described referring to FIG. 8. A case where the ultrasound transducer array 50 includes, for example, 64 ultrasound transducers 48 will be described.

Figure 8:
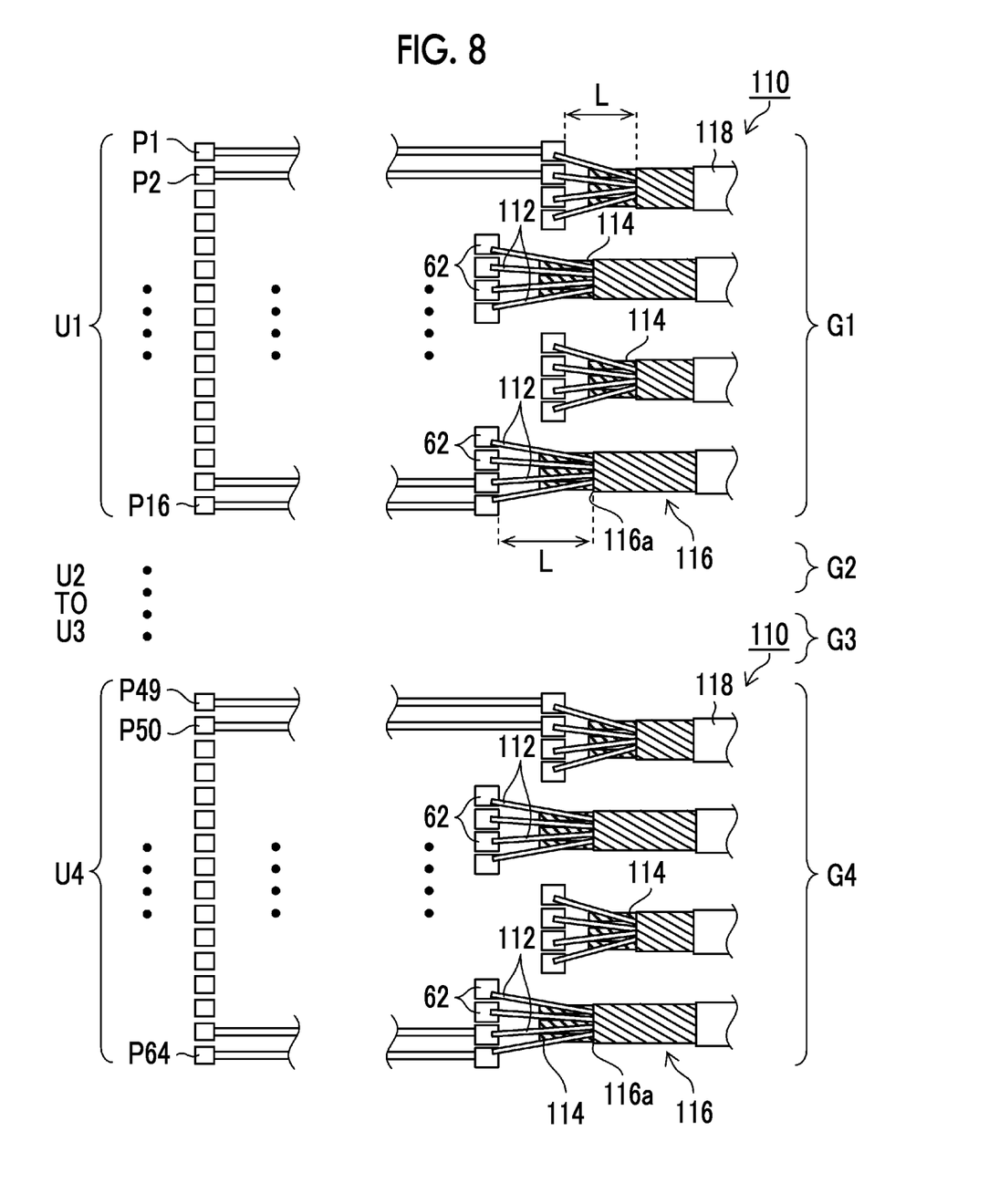
FIG. 8 is a diagram illustrating a first embodiment of a connection relationship between a plurality of ultrasound transducers and a plurality of non-coaxial cables.

As shown in FIG. 8, the 64 ultrasound transducers 48 are configured in four drive units U1, U2, U3, and U4 to be driven simultaneously. In the embodiment, one drive unit U1 includes 16 (16 channels of) ultrasound transducers 48 corresponding to P1, P2, . . . , and P16. One ultrasound beam is formed by collectively driving the 16 channels of ultrasound transducers 48. In this manner, an ultrasound beam with desired intensity can be formed. The drive unit U2 includes 16 (16 channels) ultrasound transducers 48 corresponding to P17 to P32 (not shown), the drive unit U3 includes 16 (16 channels) ultrasound transducers 48 corresponding to P33 to P48 (not shown), and the drive unit U4 includes 16 (16 channels) ultrasound transducer 48 corresponding to P49, P50, . . . , and P64.

As described above, in each signal wire 112 of the non-coaxial cable 110, a shield layer is not provided for each signal wire 112, unlike a coaxial cable. For this reason, the length of the signal wire 112 has an influence on the magnitude of electric capacity of the signal wire 112. As a length (distance L) of the signal wire 112 from the distal end of the first cable bundle 116 is longer, the electric capacity is greater, and as length (distance L) of the signal wire 112 is shorter, the electric capacity is smaller. The length of the signal wire 112 has an influence on an attenuation amount of transmission and reception sensitivity. As the length (distance L) of the signal wire 112 is longer, the attenuation amount of the transmission and reception sensitivity is greater, and there is an influence on the transmission and reception sensitivity.

In the connection structure shown in FIG. 5, there are two kinds of distances L. In this situation, for example, the signal wires 112 having a short distance L are electrically connected to all the 16 channels in the drive unit U1, and the signal wires 112 having a long distance L are electrically connected to all the 16 channels in the drive unit U4.

In this case, an ultrasound beam that is generated from the ultrasound transducers 48 in the drive unit U4 is smaller than an ultrasound beam that is generated from the ultrasound transducers 48 in the drive unit U1. In the drive unit U1 and the drive unit U4, a difference in intensity of the generated ultrasound beam is increased due to the lengths of the signal wires 112. As a result, image quality deterioration (for example, unevenness) of an ultrasound image occurs.

In the first embodiment, as shown in FIG. 8, a plurality of signal wires 112 of the respective first cable bundles 116 are connected to a plurality of electrode pads 62 electrically connected to the drive unit U1 to configure a signal wire group G1. In the first embodiment, a plurality of signal wires 112 in each first cable bundle 116 have an equal length (distance L).

The signal wires 112 have two kinds of lengths between the first cable bundles 116. That is, in a unit of the first cable bundle 116, the signal wires 112 have an equal length. The signal wire group G1 comprises two kinds of first cable bundles 116 including the signal wires 112 different in length (different in distance L) from the distal end.

The signal wire groups G2, G3, and G4 connected to a plurality of electrode pads 62 in the drive units U2, U3, and U4 similarly also include two kinds or more of signal wires 112 (having two kinds of distances L) different in length of the distal end from the first cable bundle 116.

In the signal wire groups G1, G2, G3, and G4, the signal wires 112 may have two kinds or more of lengths.

For example, the signal wire group G1 is configured with two kinds of first cable bundles of the first cable bundle 116 including the short signal wires 112 and the first cable bundle 116 including the long signal wires 112.

Since each of the signal wire groups G1, G2, G3, and G4 includes the signal wires 112 having two kinds or more of lengths (distances L), it is possible to reduce a difference in intensity of the generated ultrasound beam among the drive units U1, U2, U3, and U4. As a result, it is possible to suppress deterioration of image quality of an ultrasound image.

Figure 9:
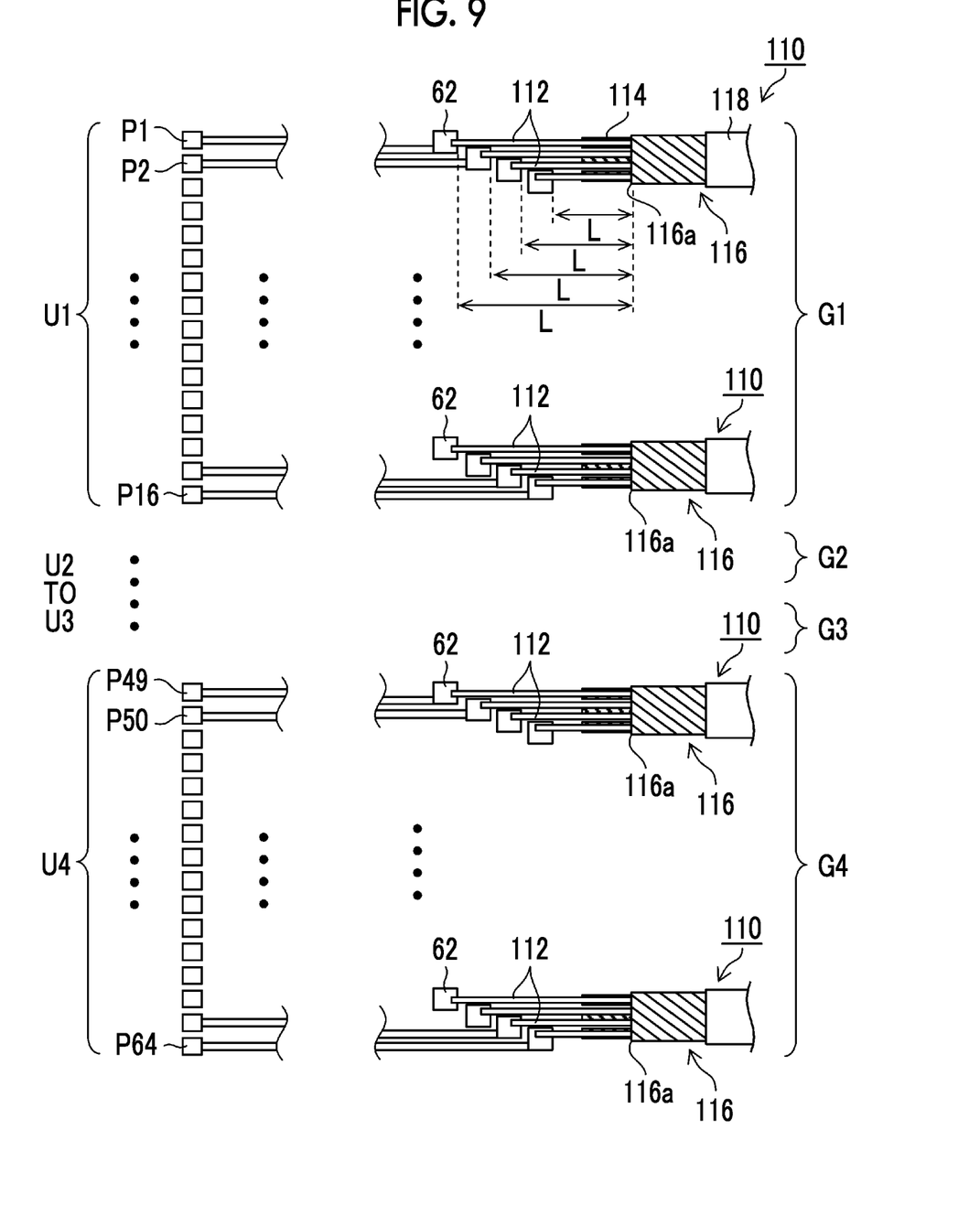
FIG. 9 is a diagram illustrating a second embodiment of a connection relationship between a plurality of ultrasound transducers and a plurality of non-coaxial cables.

Next, a second embodiment of a connection relationship between a plurality of ultrasound transducers 48 and a plurality of non-coaxial cables 110 will be described referring to FIG. 9. The same configurations as those in the first embodiment are represented by the same reference numerals, and description thereof may not be repeated.

In a signal wire group G1 of the second embodiment, four signal wires 112 in the first cable bundle 116 have different lengths. All the four signal wires 112 of the first cable bundle 116 have different lengths. Similarly, in signal wire groups G2, G3, and G4, all the four signal wires 112 of the first cable bundle 116 have different lengths. That is, in plan view, a plurality of electrode pads 62 corresponding to the first cable bundle 116 are disposed sequentially shifted along a longitudinal axis direction (a direction along the side 60b) (not shown) of the cable. Note that all the lengths of the signal wires 112 included in the first cable bundle 116 of each of the signal wire groups G1, G2, G3, and G4 do not need to be different, and the first cable bundle 116 may include the signal wires 112 having at least two kinds of lengths.

Since the signal wire groups G1, G2, G3, and G4 of the second embodiment includes the signal wires 112 having two kinds or more of lengths (distances L), as in the first embodiment, it is possible to reduce a difference in intensity of the generated ultrasound beam among the drive units U1, U2, U3, and U4. As a result, it is possible to suppress deterioration of image quality of an ultrasound image.

Figure 10:
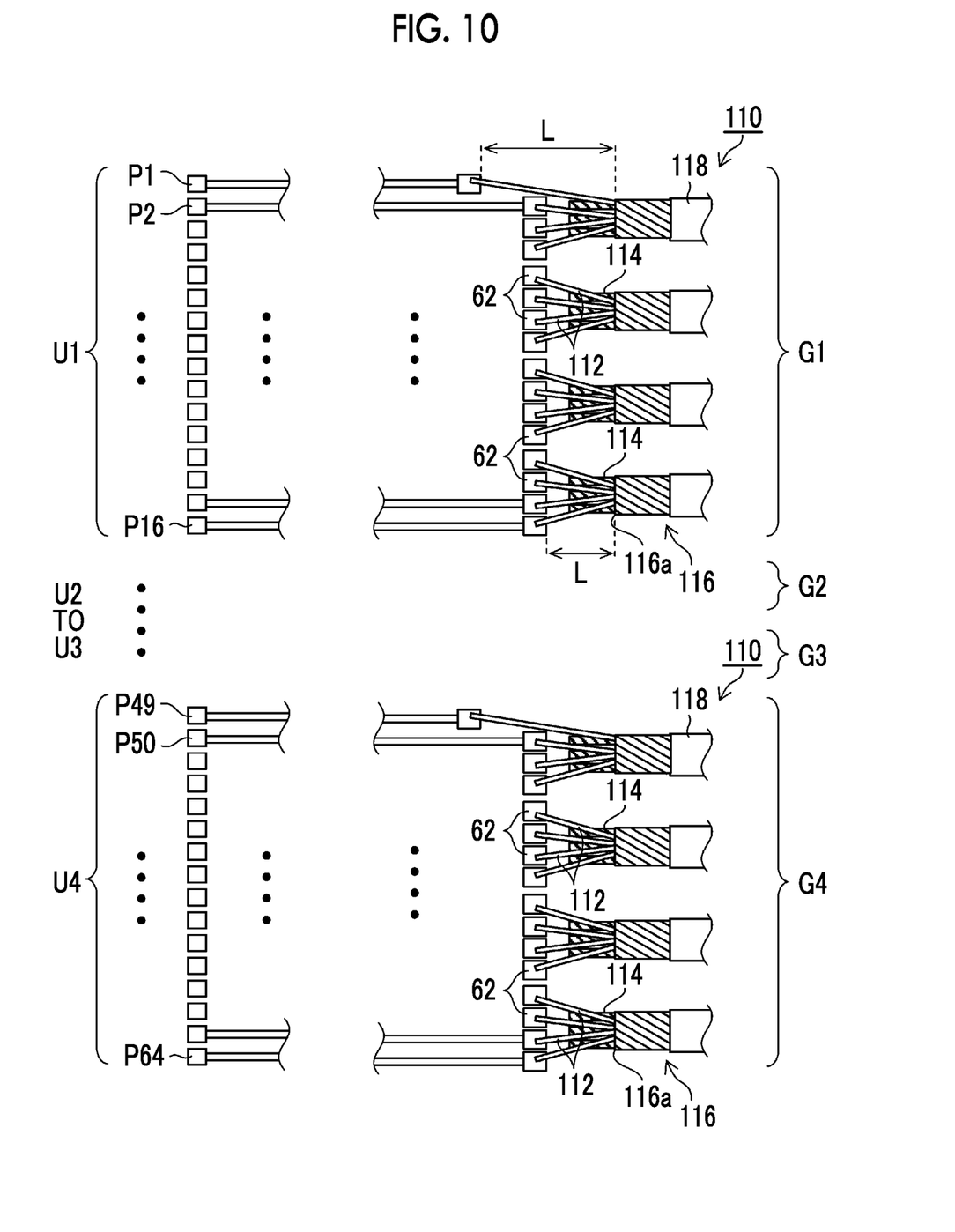
FIG. 10 is a diagram illustrating a third embodiment of a connection relationship between a plurality of ultrasound transducers and a plurality of non-coaxial cables.

Next, a third embodiment of a connection relationship between a plurality of ultrasound transducers 48 and a plurality of non-coaxial cables 110 will be described referring to FIG. 10. The same configurations as those in the first embodiment and the second embodiment are represented by the same reference numerals, and description thereof may not be repeated.

A signal wire group G1 of the third embodiment comprises a plurality of first cable bundles 116, and one first cable bundle 116 comprises at least one signal wire 112 having a different length. The signal wire group G1 comprises the signal wires 112 having the same length, excluding one signal wire 112 having a different length. Similarly, the signal wire groups G2, G3, and G4 comprise a plurality of first cable bundles 116, and one first cable bundle 116 comprises at least one signal wire 112 having a different length. The signal wire group G1 includes the signal wires 112 having at least two kinds of lengths.

Since the signal wire groups G1, G2, G3, and G4 of the third embodiment includes the signal wires 112 having two kinds or more of lengths (distances L), as in the first embodiment, it is possible to reduce a difference in intensity of the generated ultrasound beam among the drive units U1, U2, U3, and U4. As a result, it is possible to suppress deterioration of image quality of an ultrasound image.

Although the invention has been described, the invention is not limited to the above-described example, and various improvements or modifications may be of course made without departing from the spirit and scope of the invention.

EXPLANATION OF REFERENCES

10: ultrasonography system
12: ultrasound endoscope
14: ultrasound processor device
16: endoscope processor device
18: light source device
20: monitor
21a: water supply tank
21b: suction pump
22: insertion part
24: operating part
26: universal cord
28a: air and water supply button
28b: suction button
29: angle knob
30: treatment tool insertion port
32a: connector
32b: connector
32c: connector
34a: air and water supply tube
34b: suction tube
36: ultrasound observation part
38: endoscope observation part
40: distal end part
41: exterior member
42: bending part
43: flexible part
44: treatment tool lead-out port
45: treatment tool channel
46: ultrasound transducer unit
47: laminate
48: ultrasound transducer
49: piezoelectric body
50: ultrasound transducer array
52: electrode
52a: individual electrode
52b: transducer ground
54: backing material layer
55: internal space
56: coaxial cable
60: substrate
60a: side
60b: side
60c: side
62: electrode pad
64: ground electrode pad
76: acoustic matching layer
78: acoustic lens
80: filler layer
82: observation window
84: objective lens
86: solid-state imaging element
88: illumination window
90: cleaning nozzle
92: wiring cable
100: cable
102: outer coat
104: second cable bundle
106: resin layer
108: second shield layer
110: non-coaxial cable
112: signal wire
112a: conductor
112b: insulating layer
114: ground wire
116: first cable bundle
116a: distal end
118: first shield layer
130: fixing part
G1: signal wire group
G2: signal wire group
G3: signal wire group
G4: signal wire group
U1: drive unit
U2: drive unit
U3: drive unit
U4: drive unit

What is claimed is:

1. An ultrasound endoscope comprising:
an insertion part that includes a distal end part having an ultrasound transducer array in which a plurality of ultrasound transducers are arranged;
a cable that is inserted into the insertion part;
and a substrate that electrically connects the plurality of ultrasound transducers and the cable, and is disposed in the distal end part,
wherein the cable comprises: a plurality of non-coaxial cables; a second cable bundle configured to bundle the plurality of non-coaxial cables; and an outer coat configured to cover the second cable bundle,
each of the plurality of non-coaxial cables comprises:
a first cable bundle having a plurality of signal wires and a plurality of ground wires; and a first shield layer configured to coat the first cable bundle,
the substrate includes a plurality of electrode pads via which the plurality of ultrasound transducers and the plurality of signal wires respectively led out from the plurality of first cable bundles are connected,
the plurality of ultrasound transducers are divided into a plurality of drive units, wherein ultrasound transducers to be driven simultaneously are assigned to the same drive unit,
signal wires of the plurality of first cable bundles are divided into a plurality of signal wire groups corresponding to the plurality of drive units of the plurality of ultrasound transducers, and
in each of the plurality of signal wire groups, signal wires connected to electrode pads corresponding to each of the plurality of drive units, have at least two kinds of length from distal ends of the plurality of first cable bundles.

2. The ultrasound endoscope according to claim 1, wherein, in the signal wire group, the signal wires in each first cable bundle have an equal length, and the signal wires have two kinds or more of lengths between the first cable bundles.

3. The ultrasound endoscope according to claim 1, wherein, in the signal wire group, the signal wires in each first cable bundle have two kinds or more of different lengths.

4. The ultrasound endoscope according to claim 3, wherein all the signal wires in each first cable bundle have different lengths.

5. The ultrasound endoscope according to claim 1, wherein the signal wire group includes at least one signal wire having a different length.

6. The ultrasound endoscope according to claim 1, wherein the cable includes a second shield layer with which the second cable bundle is coated, inside the outer coat.

7. The ultrasound endoscope according to claim 6,
wherein the cable includes a resin layer with which the second cable bundle is coated, between the second cable bundle and the second shield layer.

8. The ultrasound endoscope according to claim 1,
wherein the cable includes a resin layer with which the second cable bundle is coated, inside the outer coat.

9. The ultrasound endoscope according to claim 7,
wherein the resin layer is a fluorine-based resin layer.

10. The ultrasound endoscope according to claim 1,
wherein the plurality of ultrasound transducers are divided for each ultrasound beam formed by collectively driven ultrasound transducers.

* * * * *